(12) United States Patent
Vecellio-None

(10) Patent No.: US 9,713,686 B2
(45) Date of Patent: Jul. 25, 2017

(54) INHALATION CHAMBER TO BE BUILT INTO A CIRCUIT OF A MECHANICAL-VENTILATION RESPIRATORY DEVICE

(75) Inventor: Laurent Vecellio-None, Chambray les Tours (FR)

(73) Assignees: Protecsom, Valognes (FR); Universite Francois Rabelais De Tours, Tours (FR)

( * ) Notice: Subject to any disclaimer, the term of this patent is extended or adjusted under 35 U.S.C. 154(b) by 325 days.

(21) Appl. No.: 14/344,500

(22) PCT Filed: Sep. 11, 2012

(86) PCT No.: PCT/EP2012/067715
§ 371 (c)(1),
(2), (4) Date: Mar. 12, 2014

(87) PCT Pub. No.: WO2013/037759
PCT Pub. Date: Mar. 21, 2013

(65) Prior Publication Data
US 2014/0338662 A1    Nov. 20, 2014

(30) Foreign Application Priority Data
Sep. 15, 2011 (FR) ..................... 11 58227

(51) Int. Cl.
*A61M 15/00* (2006.01)
*A61M 16/00* (2006.01)
(Continued)

(52) U.S. Cl.
CPC ...... *A61M 15/0086* (2013.01); *A61M 15/002* (2014.02); *A61M 15/009* (2013.01);
(Continued)

(58) Field of Classification Search
CPC .............. A61H 15/0086; A61H 15/002; A61H 15/009; A61H 16/0833; A61H 16/0883;
(Continued)

(56) References Cited

U.S. PATENT DOCUMENTS 5,178,138 A * 1/1993 Walstrom .......... A61M 15/0086
128/200.14
7,404,400 B2 * 7/2008 Lulla ................. A61M 15/0086
128/200.14
(Continued)

FOREIGN PATENT DOCUMENTS

FR    2980112    3/2013
WO    WO0183011    11/2011

OTHER PUBLICATIONS

Boukhettala, Poree, Diot, Vecellio "Study of the performances of a new spacer in mechanical ventilation." 19th Congress of the International Society for Aerosols in Medicine (ISAM) Apr. 6-10, 2013—Chapel Hill, United States; abstract.
(Continued)

*Primary Examiner* — Justine Yu
*Assistant Examiner* — Kathrynn Lyddane
(74) *Attorney, Agent, or Firm* — McDonnell Boehnen Hulbert & Berghoff LLP

(57) ABSTRACT

The present invention relates to the field of mechanical-ventilation devices, in particular devices that enable drugs to be fed into the airflow, generated by the ventilation device and directed to the respiratory pathways of a patient, using an aerosol dosing device and/or nebulizer. Specifically, the invention relates to an inhalation chamber (1) to be built into a circuit of a mechanical-ventilation respiratory device (100) through which a gas stream is to pass, said inhalation chamber (1) consisting of two portions on either side of the longitudinal axis (A) thereof, and comprising openings that lead into the inner space (Vi) thereof, wherein two openings
(Continued)

(10, 11) are to be connected to the circuit of the respirator, i.e. one opening (10) for the ingress of the gas stream and the other opening (11) for the egress of the gas stream, and one opening (12) that is to receive a nebulizer (2), characterized in that the openings (12, 13) for receiving the aerosol dosing device (3) and the nebulizer (2) are both provided in a single portion of said inhalation chamber (1) with respect to the longitudinal axis (A).

16 Claims, 2 Drawing Sheets

(51) Int. Cl.
  *A61M 16/14* (2006.01)
  *A61M 16/08* (2006.01)
(52) U.S. Cl.
  CPC ........ *A61M 16/00* (2013.01); *A61M 16/0057* (2013.01); *A61M 16/0816* (2013.01); *A61M 16/0833* (2014.02); *A61M 16/0883* (2014.02); *A61M 16/14* (2013.01); *A61M 16/0875* (2013.01)
(58) Field of Classification Search
  CPC ............ A61H 16/0816; A61H 16/0875; A61H 16/14; A61M 15/0086; A61M 15/002; A61M 15/009; A61M 16/0833; A61M 16/0883; A61M 16/0816; A61M 16/0875; A61M 16/14
  See application file for complete search history.

(56) References Cited

U.S. PATENT DOCUMENTS

| | | | | |
|---|---|---|---|---|
| 7,743,764 | B2* | 6/2010 | Dhuper | A61M 15/0086 128/200.14 |
| 7,849,853 | B2* | 12/2010 | Grychowski | A61M 15/0086 128/200.14 |
| 2006/0120968 | A1* | 6/2006 | Niven | A61M 15/0086 424/45 |
| 2011/0108025 | A1* | 5/2011 | Fink | A61M 11/005 128/200.16 |

OTHER PUBLICATIONS

Boukhettala, Diot, Poree, Vecellio "Study Of The Effectiveness Of A New Inhalation Chamber In Invasive Mechanical Ventilation" Poster ATS May 2012, San-Francisco.

N. Boukhettala ; "Study Of The Effectiveness Of A New Inhalation Chamber In Invasive Mechanical Ventilation" ATS 2012 * San Francisco—ATS International Conference; May 18-23, 2012 San Francisco, California.

Boukhettala, et al., "In Vitro Performance of Spacers for Aerosol Delivery during Adult Mechanical Ventilation", Journal of Aerosol Medicine and Pulmonary Drug Delivery, vol. 27, No. 0, pp. 1-7, (2014).

* cited by examiner

INHALATION CHAMBER TO BE BUILT INTO A CIRCUIT OF A MECHANICAL-VENTILATION RESPIRATORY DEVICE

CROSS REFERENCE TO RELATED APPLICATIONS

This application is a US National Phase application under 35 USC §371 of PCT/EP2012/067715, filed Sep. 11, 2012, which claims priority from and the benefit of French Application No. 11/58227, filed Sep. 15, 2011, the specifications of which are hereby incorporated by reference in their entirety.

The present invention relates to mechanical ventilation devices, such as devices for feeding drugs into the air flow that is generated by the ventilation device and directed to the respiratory pathways of a patient by means of an inhaler and/or a nebulizer. More precisely, the invention relates to an inhalation chamber to be built into a mechanical ventilation respiratory device, and to the device itself.

In the field of mechanical ventilation, aerosol drug delivery is used increasingly as a route of administration, especially for patients suffering from chronic obstructive pulmonary disease (COPD), asthma or chronic obstructive respiratory failure. For example, bronchodilators are drugs which are prescribed as aerosol during mechanical ventilation. Other drug classes are administered as aerosol. As such, high-dose antibiotics are a new area of research in the treatment of serious pulmonary infections. Mechanical ventilation creates a particular situation for generating and transporting aerosol in order to reach lung parenchyma.

In a MDI (Metered Dose Inhaler) or pMDI (pressurized Metered Dose Inhaler), the medicine is in a liquid suspension that can be pressurized using a propulsion gas. Inhalers are possibly the system for generating aerosol that is the best suited to administer drugs such as beta 2 adrenergic agonists or anticholinergics in mechanical ventilation when treating obstructive syndromes. A drawback of using inhalers is the necessity of synchronizing administration of the aerosol and inhalation of the patient. In mechanical ventilation, synchronizing administration must be done with the first phase of the respiratory cycle too. Using an inhalation chamber improves performance of the inhaler.

Inhalation chambers work as braking volumes in which particles ejected from the inhaler can slow down due to friction. There is a four- to six-fold increase in lung deposition using an inhalation chamber, compared to when none is used. Optimal lung deposition is obtained when the inhaler and its inhalation chamber are placed 15 cm away from the endotracheal tube.

Nebulizers are interesting in that they can be used to administer a variety of liquid drugs, not only bronchodilators, but also drugs that are not available for inhalers, such as antibiotics. Among the various types of nebulizers currently on the market, vibrating mesh nebulizers are known as the most efficient. This is a new generation of nebulizers designed for mechanical ventilation. This nebulizer allows nebulizing the whole volume that is introduced in the reservoir with no substantial increase of the solution temperature. Being ergonomic and compact, it is among the preferred nebulizing systems in mechanical ventilation.

Generally speaking, when a nebulizer and an inhaler are used, the inhaler is connected to an inhalation chamber and the nebulizer is connected to a Y-shaped piece. The practitioner must connect/disconnect successively these different elements on the ventilation circuit. There are known mechanical-ventilation devices that include on the air flow path between the respirator, which expels air, and the endotracheal tube, which brings air into the patient, an inhalation chamber, also known as spacer, on which both a nebulizer and an inhaler can be connected. Such a device is described in the patent application WO 01/83011. The inhalation chamber described therein comprises a rigid oval-shaped ball having air entry and exit positioned at opposite ends on the median longitudinal axis which separate the chamber in two portions, an upper portion and a lower portion. The air entry and exit are adapted to the tubing of a respirator or of a mechanical ventilation system. The inhalation chamber comprises two openings for connecting an inhaler and a nebulizer, respectively. The opening designed for connecting the inhaler is located in the upper portion of the chamber, whereas the one designed for connecting the nebulizer is located in the lower portion. The openings for the nebulizer and the inhaler are at opposite locations.

Such a device is not entirely satisfying. Indeed, the particles delivered by the nebulizers generally have a strong tendency to sediment in the inhalation chamber. This is increased by the fact that the nebulizer is connected to the lower part of the chamber when in use.

The U.S. Pat. No. 5,178,138 describes a mechanical-ventilation system designed for connecting both a nebulizer and an inhaler. The ventilation system comprises an inhalation chamber on which the inhaler is connected. The nebulizer is not connected to the inhalation chamber, but rather to a T-shaped piece which is itself linked to the inhalation chamber.

This type of device is not optimal either. Indeed, the nebulizer generates a particle flow along a vertical axis and the braking distance in the device is not sufficient to avoid deposition by impactation of the particles on the walls of the T-shaped piece.

Moreover, the devices in the state of the art do not allow optimizing the delivery of the substances in the inhaler. In fact, the latter generates a flow along a horizontal projection axis. There is therefore a need to increase the braking distance to avoid deposition of particles by impactation on the walls of the inhalation chamber.

Furthermore, ventilating the inhalation chamber using air coming from the respirator enables transporting aerosol outside the inhalation chamber. The shape of the inhalation chamber is therefore an element which is important to take into account to avoid zones that would be badly ventilated due to air re-circulation.

The object of the present invention is to propose a mechanical-ventilation device comprising an inhalation chamber for drug delivery by both a nebulizer and an inhaler, and that reduces, or even eliminates, the aforementioned disadvantages such as deposition by impactation and/or substance sedimentation in the inhalation chamber.

The invention therefore relates to an inhalation chamber to be built into a circuit of a mechanical-ventilation respiratory device and to be crossed by a gas stream, said inhalation chamber being composed of two portions on both sides of a longitudinal axis thereof and comprising openings which open on an internal volume thereof, comprising two openings for connection with the circuit of the respirator, one for entry of the gas stream, one for exit of the gas stream, an opening being for receiving a pressurized metered-dose inhaler and an opening for receiving a nebulizer, characterized in that the openings for receiving the inhaler and the nebulizer are both comprised on the same portion of said inhalation chamber with respect to the longitudinal axis.

Providing the openings for receiving the inhaler and the nebulizer side-to-side rather than face-to-face allows avoiding the deposition of particles by impactation, for example as produced by the nebulizer on the inhaler or vice versa.

The inhalation chamber, according to the invention, also allows connecting a metered-dose inhaler and a nebulizer simultaneously. It allows simplifying the clinical practice, since it is no more necessary to disconnect one to use the other. The practitioner gains time and the risks for the patient are reduced.

According to an aspect of the invention, the common portion in which the openings for receiving the inhaler and the nebulizer are provided on the upper portion of the chamber when built into a mechanical-ventilation respiratory device in operation. When the nebulizer is connected to the inhalation chamber in its upper portion, i.e., on the top of the chamber when it is in operation, the particles that are introduced have more time to sediment than if they were introduced from the bottom of the chamber as for the inhalation chambers in the state of the art, which allows limiting losses by sedimentation.

According to the invention, the phrase "upper portion of the chamber" is intended to designate the portion of the chamber located above the longitudinal axis of the chamber in operation in a mechanical-ventilation device, or the portion which is above the gas stream crossing the chamber operated in a working mechanical-ventilation device.

Advantageously, the inhalation chamber further comprises two frustoconical portions, the large bases thereof being common, the small bases thereof being extended by cylindrical portions, one of the cylindrical portions being in communication with the entry for the gas stream, and another one being in communication with the exit for the gas stream.

The shape of the inhalation chamber plays a role in the deposition of particles on the inner walls. A cylinder-shaped chamber, for example, would lead to an increase of this effect, resulting from a poor ventilation of the chamber. The shape of the chamber according to the invention is particularly adapted to aerosol diffusion and limits deposition by impactation. Using conical shapes or the equivalent ensures good transportation of the aerosol outside of the chamber and limits air recirculation zones, i.e., zones resulting in a bad ventilation of the chamber.

The inhalation chamber can be made of two sections, symmetrical or not.

According to an embodiment, the slope of one of the frustoconical portions, preferably of the frustoconical portion closer to the entry for the gas stream, is steeper and shorter than that of the frustoconical portion closer to the exit for the gas stream. In this embodiment, the frustoconical portion in communication with the air entry, has a smaller volume than the frustoconical portion in communication with the air exit, when the chamber is connected to the ventilation device in operation. Advantageously, the opening for receiving the nebulizer is located in the larger section of the inhalation chamber. Preferably, the opening for receiving the nebulizer is located at least 4 cm away from the opposite chamber wall.

When the nebulizer is connected to the inhalation chamber in its upper portion and in its larger section, the particles introduced along a vertical projection axis have a braking distance limiting or avoiding their deposition by impactation on the walls of the chamber. Similarly, this configuration further allows limiting deposition by sedimentation by increasing sedimentation time.

According to an embodiment, the axis of the opening for receiving the nebulizer forms an angle less than or equal to 90° with the longitudinal axis of the inhalation chamber.

According to an embodiment, the opening for receiving the inhaler is located in the narrower section of the inhalation chamber. Preferably, it is provided in the cylindrical portion of the chamber being in communication with the entry for the gas stream coming from the ventilation device.

This configuration offers to the flow of particles emitted by the inhaler along a horizontal axis a braking distance allowing limiting or eliminating their deposition by impactation.

According to an embodiment, the opening for receiving the nebulizer is located downstream of the opening for receiving the inhaler with respect to the entry for the gas stream, when the inhalation chamber is operated on the circuit of a mechanical-ventilation device.

Preferably, the opening for receiving the metered-dose inhaler comprises means for directing the aerosol flow along an axis which is horizontal with respect to the longitudinal axis of the inhalation chamber.

The opening for receiving the metered-dose inhaler comprises a means such as a spray nozzle which creates an obstacle in the holding chamber. The nebulizer produces liquid particles that could undergo impact when the particles meet an obstacle. When the nebulizer is located upstream of the opening for the pMDI, the particles can impact on the spray nozzle and obstruct it, since air produced by the respirator crosses the chamber unidirectionally: using it with the pMDI thus becoming impossible. The proposed solution to this problem is to locate the nebulizer downstream of the pMDI with respect the gas stream crossing the chamber.

Advantageously, the openings for receiving the nebulizer and the inhaler comprise, respectively, a shutting means.

Indeed, when only one of the devices, either the nebulizer or the inhaler, is connected to the inhalation chamber, it is necessary to shut the opening for receiving the other device using a sealable means.

According to an aspect of the invention, the internal volume of the inhalation chamber is under 500 mL, preferably less than 300 mL. In fact, the inhalation chamber must have an internal volume less than the inspiration volume of the patient, corresponding to a standard of 500 mL.

More precisely, the internal volume of the chamber is less than the alveolar volume, which is defined as the part of the volume inspired by the patient that reaches the lungs, which is the target site for medication (inspired volume—dead space volume). The volume of the chamber must therefore be under 300 mL preferably.

Moreover, the chamber volume must be above 20 mL to ensure stocking and braking the received particles.

Therefore, the internal volume of the chamber is preferably comprised between 20 mL and 300 mL.

The invention further relates to a mechanical-ventilation respiratory device comprising:
- a respirator for insufflating a gas volume,
- at least one inhalation duct to be used by the gas stream during an inspiration phase,
- at least one exhalation duct to be used by the gas stream during an expiration phase,
- a supply duct for supplying the gas stream to the patient,
- the device being characterized in that it comprises an inhalation chamber as described above.

In such a device, well known to the skilled person, the respirator works as a gas source, generally air and/or oxygen, and comprises a unit that allows controlling ventilation parameters. Among others, it allows controlling inspiratory and expiratory phases. According to the invention, the inhalation chamber is located on the path of the gas stream that is taken during an inspiration or inhalation phase.

Again according to the invention, the entry of the gas stream of the inhalation chamber is connected to the inhalation duct, and the exit of the gas stream of the inhalation chamber is connected to the supply duct for supplying gas stream to the patient using a Y-shaped piece.

Advantageously, the inhalation chamber, the exhalation duct and the supply duct to the patient are respectively connected to the Y-shaped piece.

According to an embodiment, the supply duct is an endotracheal tube.

According to another embodiment, the supply duct is connected to a mask to be worn by a patient.

Figure 1:
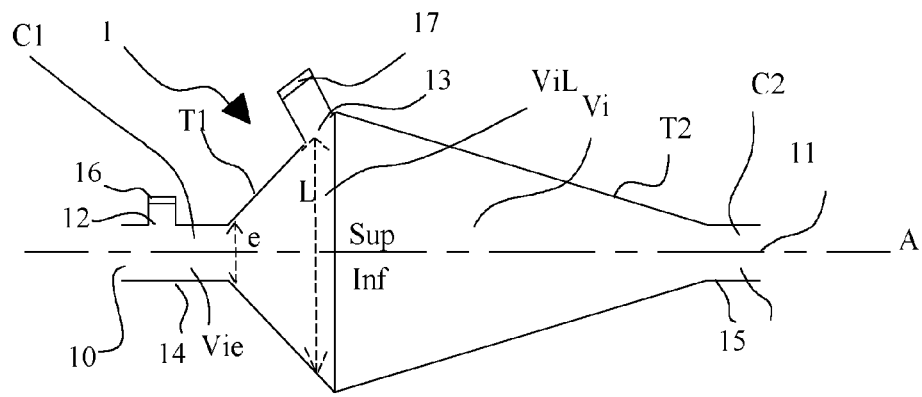
FIG. 1 is a side section view of an inhalation chamber, according to a first embodiment.

With reference to FIG. 1, there is shown an inhalation chamber 1 according to a first embodiment. The inhalation chamber 1 is, for example, made of polycarbonates, and it defines an internal volume 30 for receiving particles from the nebulizer and/or the metered-dose inhaler, and to be crossed by a gas stream generated by a mechanical-ventilation device.

The inhalation chamber 1 comprises four openings. The first opening (10) is an entry for the gas stream emitted by a mechanical-ventilation device, such as air, and the second one is an exit (11) for the same flow. These two openings are provided on the same longitudinal axis 32 of the inhalation chamber 1. The dimensions of the openings 10 and 11 are adapted to enable connection of the chamber 1 on the tubing of a conventional mechanical-ventilation device. The third opening 12 if for receiving a pressurized metered-dose inhaler (pMDI), and the fourth one is an opening 13 for receiving a nebulizer, preferably a vibrating mesh nebulizer.

The longitudinal axis 32 separates the inhalation chambers in two portions. The openings 12 and 13 are provided in a common portion of the inhalation chamber 1. When the chamber is incorporated into a mechanical-ventilation device, the common portion comprising the openings 12 and 133 is the upper portion 60 of the chamber, by opposition to the lower portion 70.

The inhalation chamber 1 further comprises two frustoconical portions 34, 35, of which the large bases are common. It defines a large section 36 of the chamber 1 in a central region of the chamber 1 in which the internal volume is greater, as well as two narrow sections in which the internal volume is smaller close to the entry 10 and the exit 11, respectively. Cylindrical portions 14, 15 extend from the small bases of the inhalation chamber 1, the cylindrical portion 14 being in communication with the entry 10 for the gas stream, the cylindrical portion 15 being in communication with the exit 10 for the gas stream.

The slope of the frustoconical portion 34 leading to the entry 10 for the gas stream is steeper and shorter the frustoconical portion 35 leading to the exit 11 for the gas stream. The opening 13 for the nebulizer is provided in the larger section 36 of the chamber 1 so that the emitted particles emerge where the internal volume is greater, noted 30.1. The axis of the opening 13 forms an angle which is less than or equal to 90° with respect to the longitudinal axis 32 of the inhalation chamber.

The opening 12 for receiving the metered-dose inhaler is provided, for its part, in a narrow section 37 of the chamber 1, preferably in the cylindrical portion 38 in communication with the entry 10 for the gas stream. In this case, the emitted particles thus emerge when the volume is smaller, noted 30.2. The volume 30.2 is smaller than the volume 30.1. Furthermore, the opening 12 is located upstream of the opening 13 to avoid that particles emitted by the nebulizer obstruct by impactation the exit opening of the metered-dose inhaler when it is connected. Therefore, the opening 13 is located on the frustoconical portion 34 but could be placed on the frustoconical portion 35.

The openings 12 and 13 comprise shutting means 16, 17, respectively, for sealably shutting them when no nebulizer and/or inhaler are connected to the inhalation chamber 1.

Figure 2:
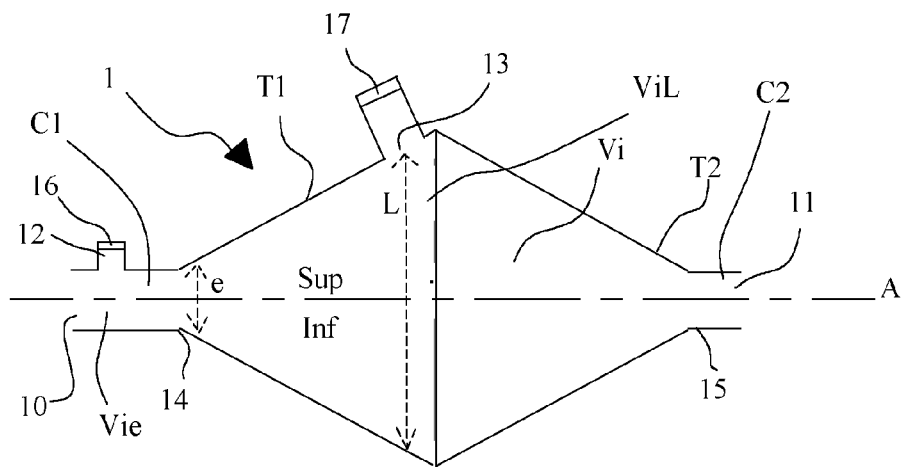
FIG. 2 is an above section view of an inhalation chamber, according to a second embodiment.

The inhalation chamber 1 represented in FIG. 2 comprises the same features as the inhalation chamber 1 represented in FIGS. 1 and 3 to 7, except the frustoconical portions 34, 35, which are, according to this embodiment, symmetric, the slopes of the frustoconical portions 34, 35 being identical.

Figure 3:
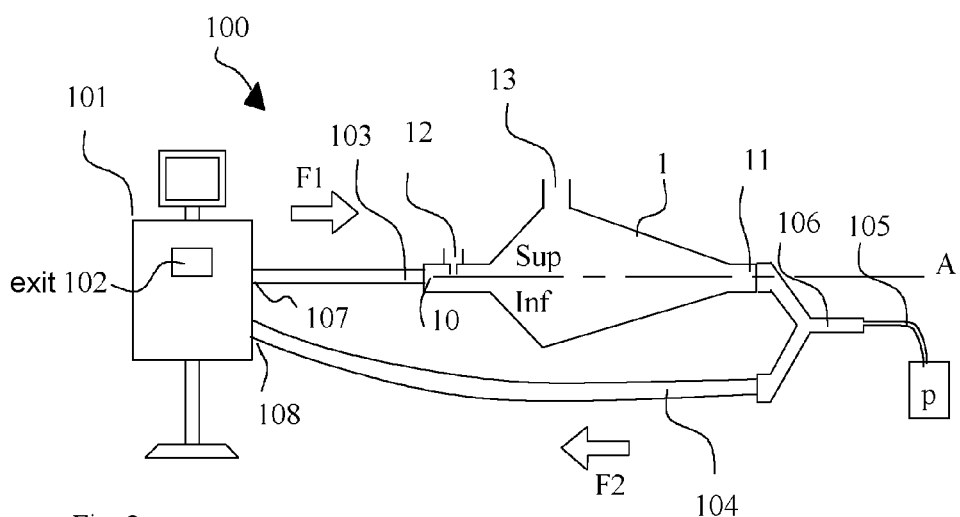
FIG. 3 is a schematic representation of a mechanical-ventilation respiratory device comprising an inhalation chamber, according to the invention.

Now referring to FIG. 3, there is shown a mechanical-ventilation respiratory device 100 in which is incorporated an inhalation chamber 1 according to the invention.

The device 100 typically comprises a respirator 101 to insufflate a gas volume to a patient 40. The respirator 101 comprises a unit 102 capable of controlling gas stream and pressure, generally an air/oxygen mixture.

The device 100 comprises an inspiration or inhalation duct 103 for being crossed by the gas stream during an inspiration or inhalation phase, and an expiration or exhalation duct for being crossed by the gas stream during an expiration (exhalation) phase, and a supply duct 105 for supplying the gas stream to the patient 40.

The inspiration duct 103 is firstly connected to an exit 107 of the respirator 101, and secondly, to an entry 10 of the inhalation chamber 1. The exit 11 of the chamber 1 is, on its part, connected to a Y-shaped piece 106, so that the inhalation chamber is located on the path taken by the gas stream during inspiration phases.

Another branch of the Y-shaped piece 106 is linked to the duct 105 connected to the patient 40. As such, the duct 105 can be replaced by a mask worn by the patient 40, depending on the situation.

The expiration duct 104 is connected, firstly, the third branch of the Y-shaped piece 106, and secondly, to an entry 108 of the respirator 101.

The inhalation chamber 1 is linked to the device 100 so that the openings 12 and 13 for connecting, respectively, the nebulizer and the metered-dose inhaler, are on the top of the chamber 1, i.e. in the upper portion 60 separated from the lower portion 70 by the longitudinal axis 32 of the chamber 1.

The device 100 thus defines a circuit for the gas stream. Arrows 50 and 51 represent the circulation of the gas stream during an inspiration phase and an expiration phase, respectively.

Figure 4:
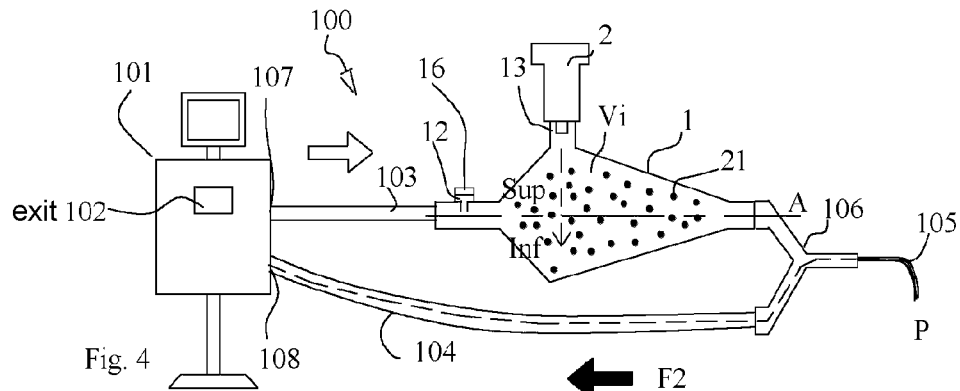
FIG. 4 is a schematic representation of a mechanical-ventilation respiratory device, during operation, comprising an inhalation chamber, according to the invention, on which is connected a nebulizer, during an expiration phase.
Figure 5:
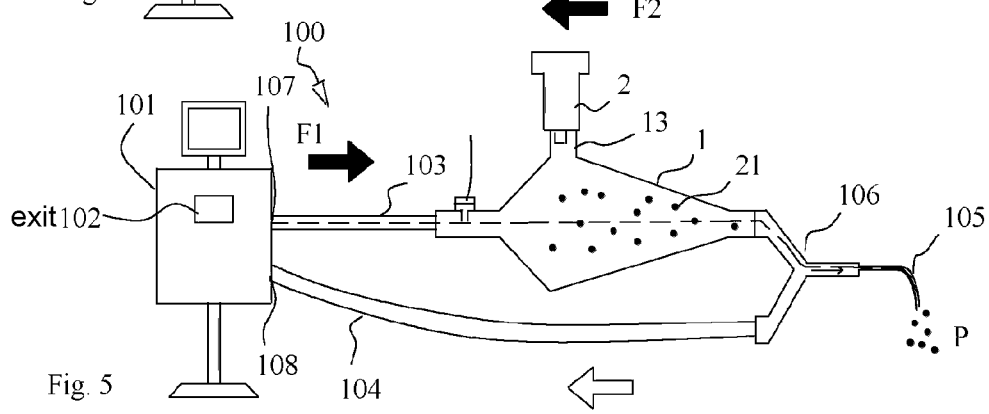
FIG. 5 is a schematic representation of a mechanical-ventilation respiratory device, during operation, comprising an inhalation chamber, according to the invention, on which is connected a nebulizer, during an inspiration phase.

In reference with FIGS. 4 and 5, there is described an inhalation chamber 1 working in a mechanical-ventilation device 100 when a nebulizer 2, such as a vibrating mesh nebulizer, is used and thus connected to the inhalation chamber 1 in its upper portion 60.

FIG. 4 represents an air expiration phase by the patient 40. The gas stream expired by the patient crosses the duct 105, takes the Y-shaped piece 106 and then the expiration duct 104 (arrow 51). The aerosol produced by the nebulizer 2 is stocked in the inhalation chamber 1. To do so, the nebulizer 2 is operated and the nebulized particles enter the internal volume 30 of chamber 1 along a vertical projection axis. The particles being projected in the larger section of the chamber, the volume 30.1 is sufficient to limit their deposition by impactation against the walls of the chamber, or their sedimentation.

During the next inspiration phase (FIG. 5), the gas stream (arrow 3) takes the inspiration duct 103 from the respirator 101 and crosses the inhalation chamber 1, dragging along nebulized particles 21 towards the patient 40 using the Y-shaped piece 106 and tube 105.

The opening 12 for receiving the inhaler is closed by shutting means 16, which is sealable.

Figure 6:
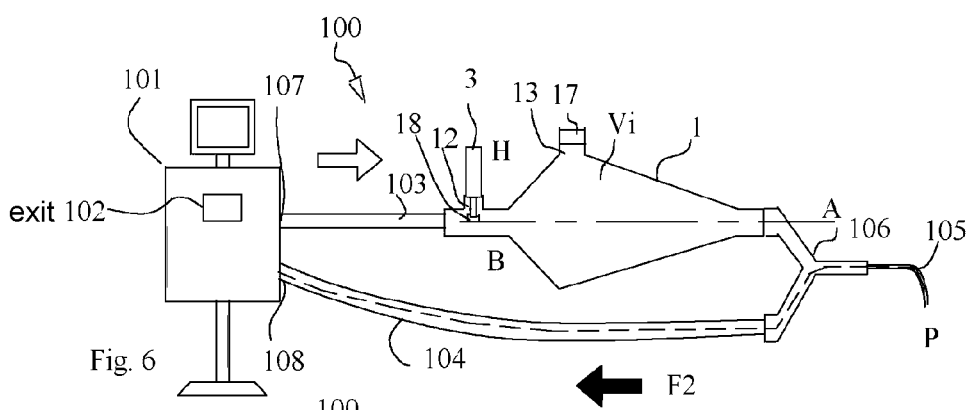
FIG. 6 is a schematic representation of a mechanical-ventilation respiratory device, during operation, comprising an inhalation chamber, according to the invention, on which is connected an inhaler, during an expiration phase.
Figure 7:
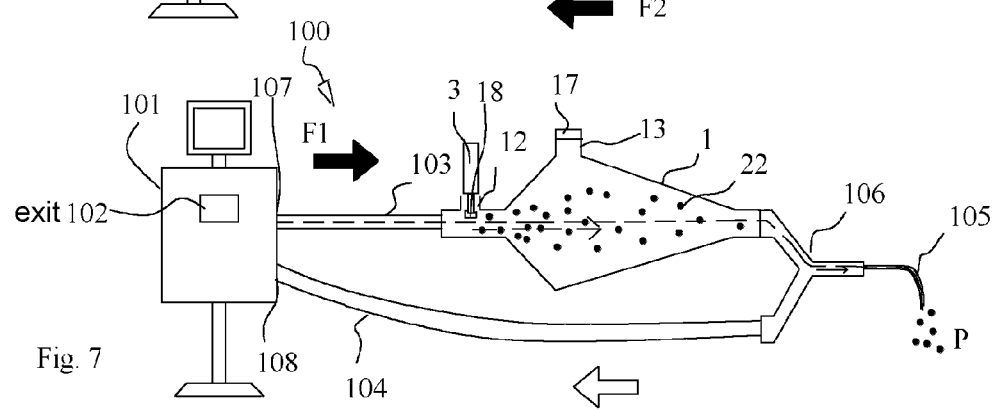
FIG. 7 is a schematic representation of a mechanical-ventilation respiratory device, during operation, comprising an inhalation chamber, according to the invention, on which is connected an inhaler, during an inspiration phase.

Now referring to FIGS. 6 and 7, there is described an inhalation chamber 1 working in a mechanical-ventilation device 100 when an inhaler 3 is used and thus connected to the inhalation chamber 1 on the opening 12.

FIG. 6 represents an air expiration phase by the patient 40. During this expiration phase, everything works as explained with reference to FIG. 4, with the difference that no particle produced by the metered-dose inhaler 3 is stocked in the inhalation chamber 1.

At the beginning of the next inspiration phase, the inhaler 3 is manually started by a practitioner. After starting, particles enter the internal volume 30 of the chamber 1 along a horizontal projection axis. Indeed, the opening 12 comprises means for directing the aerosol flow along an axis horizontal with respect to the axis 32 of the inhalation chamber 18, such as a spraying nozzle.

The particles being projected along a horizontal axis, and thus parallel to the longitudinal axis 32 of the chamber 1, in a narrow section 37 of the chamber 1 and close to the entry 10 for the gas stream, the volume 30 is sufficient to limit their deposition by impactation against the walls of the chamber, or their sedimentation.

The gas stream that is generated by the respirator 101 takes the inspiration duct 103 and then crosses the inhalation chamber 1, dragging along particles 22 towards the patient 40 using the Y-shaped piece 106 and tube 105.

It is of course possible to simultaneously use a metered-dose inhaler and a nebulizer during the same respiratory cycle. Since the nebulizer is located downstream of the inhaler, the particles produced by the nebulizer cannot impact themselves on the inhaler.

Furthermore, the inhalation chamber as described with reference to FIG. 2 in a mechanical-ventilation respiratory device works identically as described with reference to FIGS. 4 to 7.

Therefore, the invention is particularly advantageous, since it allows simplifying the clinical practice of the practitioner and limiting the risks that are induced by intervening on the circuit of a patient to connect the nebulizer and the metered-dose inhaler. The invention also allows increasing the performance of metered-dose inhalers and nebulizers, thus improving efficiency of the treatment. Moreover, the invention is economically interesting since it allows administering a greater quantity of medicine to the patient and to reduce the cost of connectors by using a unique connector, compared to the two that are currently used for the metered-dose inhaler and the nebulizer.

The invention claimed is:

1. An inhalation chamber (1) to be built into a circuit of a mechanical-ventilation respiratory device (100) and to be crossed by a gas stream, the inhalation chamber (1) comprising an upper portion on a side of a longitudinal axis (32) and a lower portion on an other side of the longitudinal axis (32) and comprising a first opening, a second opening, a third opening, and a fourth opening, which open on an internal volume (30), the first and the second opening (10, 11) being for connection with a circuit of a respirator and defining the longitudinal axis therebetween, the first opening (10) for entry of a gas stream, the second opening (11) for exit of the gas stream, the third opening (12) for receiving a pressurized metered-dose inhaler (3) and the fourth opening (13) for receiving a nebulizer (2), the chamber having sections of which one larger section (36) has a width (L) greater than widths of all other sections of the inhalation chamber, and one narrower section (37) has a narrower width (e) than the larger section, the third opening (12) being provided in the narrower section (37) and the fourth opening (13) being provided in the larger section (36), wherein the third and the fourth openings (12, 13) for receiving the inhaler (3) and the nebulizer (2) are both entirely comprised on a same one of the upper and the lower portion of the inhalation chamber (1) with respect to the longitudinal axis (32), and wherein the fourth opening (13) is located downstream of the third opening (12) with respect to the longitudinal axis (32).

2. The inhalation chamber of claim 1, wherein the upper portion of said inhalation chamber (1) comprises the third and fourth openings (12, 13) for receiving the inhaler (3) and the nebulizer (2).

3. The inhalation chamber of claim 1, wherein the upper portion and the lower portion form the inhalation chamber comprising two frustoconical portions (34, 35), wherein each large bases of the frustoconical portions (34, 35) are common, and a cylindrical portion (38, 39) extends from a small base of each frustoconical portion (34, 35), one of the cylindrical portions (38) being in communication with the first opening (10) for entry of the gas stream, and the other cylindrical portion (39) being in communication with the second opening (11) for exit the gas stream.

4. The inhalation chamber of claim 1, wherein the fourth opening (13) for receiving the nebulizer (2) is located downstream of the third opening (12) for receiving the inhaler (3) with respect to the first opening (10) for entry of the gas stream.

5. The inhalation chamber of claim 3, wherein the frustoconical portion (34) closer to the first opening (10) for entry of the gas stream has a slope from its large base to its small base at an angle steeper and at a length shorter than that of the frustoconical portion (35) closer to the second opening (11) for exit of the gas stream.

6. The inhalation chamber of claim 1, wherein the third and the fourth openings (12, 13) are for receiving the inhaler (3) and the nebulizer (2), wherein the third and the fourth openings each comprise shutting means (17, 16).

7. The inhalation chamber of claim 1, wherein an axis of the fourth opening (13) for receiving the nebulizer (2) forms an angle less than or equal to 90° with the longitudinal axis (32) of the inhalation chamber (1).

8. The inhalation chamber of claim 1, wherein the third opening (12) for receiving the inhaler (3) comprises means (18) for directing an aerosol flow along an axis which is horizontal with respect to the longitudinal axis (32) of the inhalation chamber (1).

9. The inhalation chamber of claim 1, wherein the internal volume (30) is less than 500 mL.

10. The inhalation chamber of claim 1, wherein the internal volume (30) is less than 300 mL.

11. A mechanical-ventilation respiratory device (100) comprising:
   (a) an inhalation chamber (1) comprising an upper portion on a side of a longitudinal axis (32) and a lower portion on an other side of the longitudinal axis (32) and comprising a first opening, a second opening, a third opening and a fourth opening which open on an internal volume (30), the first and the second opening (10, 11) being for connection with a circuit of a respirator, the first opening (10) for entry of a gas stream, the second opening (11) for exit of the gas stream, the third opening (12) for receiving a pressurized metered-dose inhaler (3) and the fourth opening (13) for receiving a nebulizer (2), the chamber having sections of which one larger section (36) has a width (L) greater than widths of all other sections of the inhalation chamber, and one narrower section (37) has a narrower width (e) than the larger section, the third opening (12) being provided in the narrower section (37) and the fourth opening (13) being provided in the larger section (36), wherein the third and fourth openings (12, 13) for receiving the inhaler (3) and the nebulizer (2) are both entirely comprised on a same one of the upper portion and the lower portion of the inhalation chamber (1) with respect to the longitudinal axis (32), and wherein the fourth opening (13) is located downstream of the third opening (12) with respect to the longitudinal axis (32);
   (b) a respirator (101) for insufflating a gas volume, comprising an exit (102) and an entry (101) for a gas stream;
   (c) an inhalation duct (103) connected to the exit (102) for the gas stream;
   (d) an exhalation duct (102) connected to the entry (103) for the gas stream; and
   (e) a supply duct (105) for supplying the gas stream to a patient (40).

12. The mechanical-ventilation respiratory device (100) of claim 11, wherein the inhalation chamber (1) is located on a path of the gas stream during an inhalation phase.

13. The mechanical-ventilation respiratory device (100) of claim 11, wherein the first opening (10) for entry of the gas stream in the inhalation chamber (1) is connected to the inhalation duct (102) and the second opening (11) for exit of the gas stream from the inhalation chamber (1) is connected to the supply duct (105) for supplying the gas stream to the patient by means of a Y-shaped piece (106).

14. The mechanical-ventilation respiratory device (100) of claim 13, wherein the Y-shaped piece (106) is connected to the inhalation chamber (1), to the exhalation duct (104), and to the supply duct (105) connected to the patient (40).

15. The mechanical-ventilation respiratory device (100) of claim 11, wherein the supply duct (105) to the patient (40) is an endotracheal tube.

16. The inhalation chamber of claim 1, wherein the internal volume (30) comprised between 20 mL and 300 mL.

* * * * *